United States Patent [19]

Mayo et al.

[11] Patent Number: 4,930,513

[45] Date of Patent: Jun. 5, 1990

[54] TWO DIMENSIONAL PROCESSING OF PULSED DOPPLER SIGNALS

[75] Inventors: William T. Mayo, Seal Beach; Paul M. Embree, Irvine, both of Calif.

[73] Assignee: U.S. Philips Corporation, New York, N.Y.

[21] Appl. No.: 224,106

[22] Filed: Jul. 26, 1988

[51] Int. Cl.⁵ ............................................... A61B 8/00
[52] U.S. Cl. .............................. 128/661.09; 73/861.25
[58] Field of Search ...................... 128/661.07, 661.08, 128/661.09, 661.1; 73/861.25; 367/90; 364/726

[56] References Cited

U.S. PATENT DOCUMENTS

| | | | |
|---|---|---|---|
| 4,328,555 | 5/1982 | Nussbaumer | 364/726 |
| 4,601,006 | 7/1986 | Liu | 364/726 |
| 4,646,099 | 2/1987 | Apostolos | 364/726 X |
| 4,770,184 | 9/1988 | Greene, Jr. et al. | 128/661.08 |
| 4,780,831 | 10/1988 | Iwata et al. | 364/726 X |

OTHER PUBLICATIONS

Maulik, D. et al. "Doppler Evaluation of Fetal Hemodynamics", UTS in Medicine & Biology vol. 8, No. 6, pp. 708-710 1982.

Cannon, S. R. et al., "Digital Fourier Techniques in the Diagnosis of & Quantification of Aortic Stenosis w/Pulsed Doppler Echocardiography", Jrnl of Clinical Ultrasound vol. 10 No. 3 Mar. 1982.

Greene, F. M. et al., "Computer-Based Pattern Recognition of Carotid Arterial Disease Using Pulsed Doppler Ultrasound", UTS in Medicine & Biology, vol. 8 No. 2, pp. 161-176, 1982.

Primary Examiner—Francis Jaworski
Attorney, Agent, or Firm—Jack E. Haken

[57] ABSTRACT

A processor for pulsed Doppler velocity measurement utilizes a two dimensional discrete Fourier transform to map wideband signals into a frequency space where constant velocity Doppler spectral components are represented as radial lines. A radial projection then extracts target velocity information.

16 Claims, 7 Drawing Sheets

TWO DIMENSIONAL PROCESSING OF PULSED DOPPLER SIGNALS

The invention relates to methods and apparatus for measuring velocity by analysis of Doppler shift induced in broadband pulsed waves. The invention is particularly useful in conjunction with echo ultrasound systems which measure blood flow within a human or animal body.

BACKGROUND OF THE INVENTION

Pulsed Doppler ultrasound systems are commonly used to measure and map the velocity of blood flow within human and animal bodies. Pulses of ultrasound energy are directed into the body along a path which intersects blood vessel or coronary chamber. Ultrasound energy from the pulse is backscattered from blood within the vessel or chamber and returns to a transducer where it is converted into an electrical signal. If the blood has a velocity component along the direction of propagation of the ultrasound waves, the frequency of the scattered echoes will be shifted, in relation to the frequency of the incident ultrasound energy. The Doppler shift which is thus induced in the echoes can be analyzed to yield a numeric estimate of blood velocity and/or to produce a map of blood velocity as a function of position within the body.

Doppler blood flow measuring systems are often included as an adjunct or accessory function to conventional ultrasound imaging systems which map acoustic impedance as a function of position within the body. Difficulties arise, however, because ultrasound signal requirements for Doppler blood flow measurement are substantially different than those required for high resolution ultrasound imaging. Conventional Doppler spectrum analysis for ultrasound blood flow measurement requires a narrow bandwidth signal, but narrow bandwidth inherently limits the range resolution which would otherwise be obtainable in an ultrasound imaging system. Short (and thus inherently wide band) pulses of ultrasound energy are used to maximize range resolution in imaging systems while long pulses with narrow bandwidth are used for Doppler measurement in order to obtain well defined spectral shifts and high signal-to-noise ratios.

One difficulty with conventional Doppler spectrum analysis arises from the interpretation of signals based on a Doppler shift model of scattering from moving blood cells. According to this model, Doppler frequency shift is proportional to the frequency of the incident ultrasound wave before it is scattered by the blood cells. A short pulse of ultrasound energy contains a wide spectrum of incident frequencies and results in a wide spectrum of scattered signals regardless of the velocity spread of the scattering blood cells. In addition, wide band filters (which are necessary in such systems) inherently result in a lower signal-to-noise ratio than would be possible with narrow band filters.

Prior art Doppler spectra are further subject to aliasing since they are periodic with a period equal to the pulse repetition frequency. Thus, from a prior art Doppler spectrum, one can only determine the velocity modulo $(c/2)(f_p/f_O)$ where $f_p$ is the pulse rate. For example, if the RF ultrasound center frequency $f_O$ is $5 \times 10^6$ hertz and the line rate is $5 \times 10^3$ lines per second, a prior art one dimensional Doppler spectrum can only unambiguously determine velocities which are less than 0.75 meters per second (assuming the speed of sound is 1500 m/sec.).

"Ultrasonic M-mode RF Display Technique with Application to Flow Visualization" by P. M. Embree and W. T. Mayo, International Symposium on Pattern Recognition and Acoustical Imaging, Leonard A. Ferrari, Editor, Proc. SPIE 768, pp. 70–78 (1987) discusses a technique to display digitally sampled ultrasonic A-lines using false color. The RF samples of each backscattered A-lines using false color. The RF samples of each backscattered A-line are displayed vertically and consecutive A-lines are displayed side-by-side horizontally to form a two dimensional false color image. Fringe patterns in the two-dimensional image can be related to conventional Doppler processing and correlation processing concepts for fluid motion display. A rectangular section of the fringe pattern displayed in this way represents the two dimensional matrix of samples to be processed by the two dimensional Fourier technique which is the subject of this invention.

SUMMARY OF THE INVENTION

The amplitude of echoes along an ultrasound A-line are sampled at discrete times, at a rate which is above the Nyquist frequency. RF (radio frequency) sample vectors at a selected range from successive A-lines, taken in the same direction through a region of the body, form a two-dimensional matrix with element positions described by a first, fast-time variable which specifies the range of a data sample along its A-line and a second, slow-time, variable which specifies the position of the A-line within a group of collected A-lines. The data matrix is processed with a two-dimensional discrete Fourier transform taken with respect to the fast-time variable and the slow-time variable which maps the data set into a discrete two-dimensional Fourier frequency space wherein constant velocity Doppler shifts are mapped as radial lines. The slow-time axis corresponds to a slow-frequency (Doppler frequency) axis in the two-dimensional Fourier frequency space and the fast time axis corresponds to a fast frequency (radio frequency) axis in the Fourier frequency space. Echoes of wide band pulses which are scattered from moving targets are mapped as generally elliptical shapes in the two-dimensional Fourier space. The angle between the major axis of the ellipse and the coordinate axes of the Fourier space is a high quality measure of the velocity of the scattering medium.

In a preferred embodiment, the angular distribution of the spectrum in two-dimensional Fourier frequency space (and hence velocity components in the region of the object) are estimated by computing a radial projection of the transformed data array.

The discrete Fourier transform is periodic in nature. As a result, the spectral components produced by high velocity scatterers will tend to "wrap around" unit cells in the Fourier frequency space. This is the familiar "aliasing" problem associated with the Fourier transform of any sampled signal.

The radial projection technique for estimating object velocities can be used at high velocities, where the spectrum wraps around, if the projection line is wrapped around a unit cell. The two-dimensional Fourier spectra of wide band Doppler signals are highly eccentric ellipses. The radial projection of these ellipses is sharply peaked for projection directions which are parallel to the major axis of the ellipse and broadly peaked for projection directions that intersect the ellipses at other angles. As a result, radial projections provide immunity to the aliasing effects of conventional Doppler processing where aliasing spectra are identical to true spectra.

In a further preferred embodiment, the two-dimensional Fourier transform is computed from the complex envelope of A-line signals rather than from the actual radio frequency A-line echo signals. Computation from the complex envelope shifts the elliptical contours of the echo signal spectrum in Fourier space. The radial projection technique is used with complex envelope spectra by taking the projection around a point on the fast-frequency axis of Fourier space which corresponds to the RF center frequency of the incident ultrasound wave.

In conventional Doppler processing on complex envelope data, each A-line is averaged over the range gate which collapses the data array into a single row with one complex sample for each A-line. A one-dimensional discrete Fourier transform is then performed on this row to produce the Doppler spectrum. The peak of the Doppler spectrum occurs at a frequency determined by $f_{max} = (2 \text{ v}/\text{c}) f_O$, where $f_O$ is the frequency of the incident ultrasound wave, c is the velocity of sound in the medium and v is the velocity of the scatterer. Averaging over the range gate is equivalent to computing only the zero frequency component of a discrete Fourier two-dimensional transform; a prior art Doppler spectrum is only a single slice through a two-dimensional discrete Fourier transform taken along the horizontal (Doppler frequency) axis. Therefore, the two-dimensional spectrum of the present invention contains more information than a conventional one-dimensional Doppler spectrum.

Discrete Fourier transforms of random data are inherently noisy and conventional Doppler spectra will be noisy unless many samples are averaged in the range gate. This results in a loss of range resolution.

A radial projection in two-dimensional Fourier space is based on all of the information in a two-dimensional discrete Fourier transform and is inherently less noisy than a one-dimensional Doppler spectrum. As a result, the radial projection method permits one to obtain reasonable estimates of velocity using fewer samples per range gate and/or fewer A-lines than would be required for prior art Doppler processing. Thus, systems using radial projection algorithms for signal processing may have higher range resolution and/or higher time resolution than systems using prior art Doppler processing.

THE DRAWINGS

The invention will be described with reference to the attached drawings in which.

Figure 10:
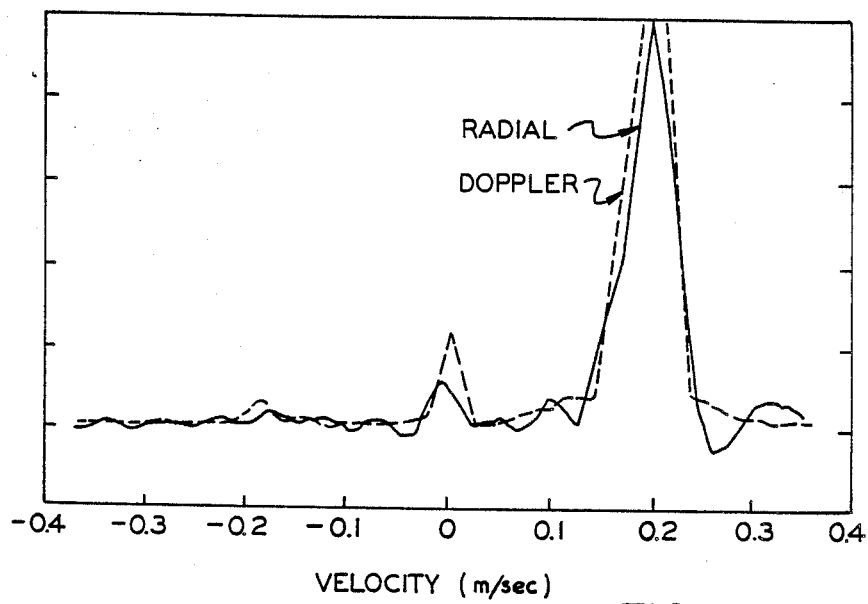
Figure 11:
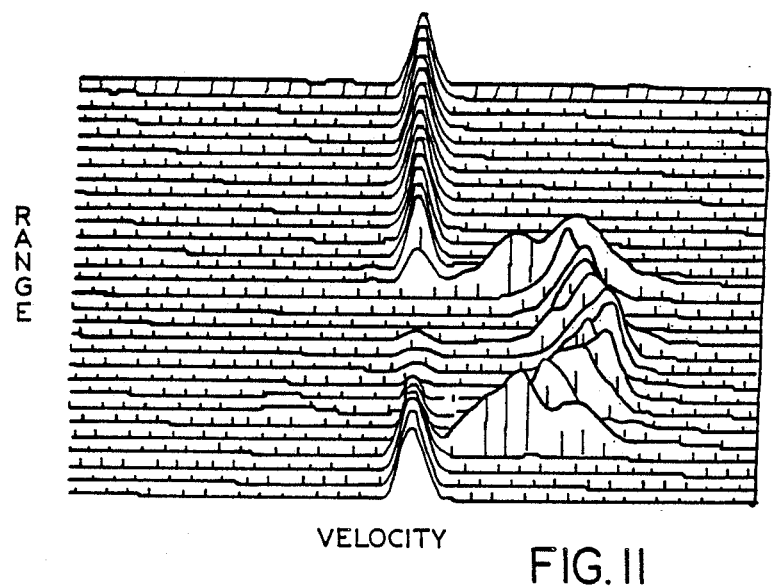
Figure 12:
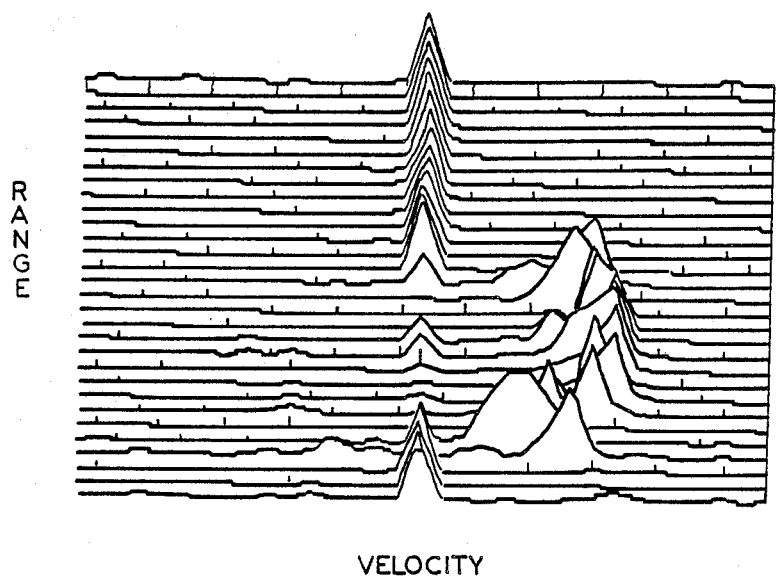

FIG. 10 compares Doppler velocity measurements derived by conventional one-dimensional Doppler techniques and by two-dimensional radial projection techniques;

FIGS. 11 and 12 respectively illustrate ranges of blood velocity measurements in a carotid artery obtained by radial projection techniques and by conventional Doppler techniques.

DESCRIPTION OF THE PREFERRED EMBODIMENTS

Figure 1:
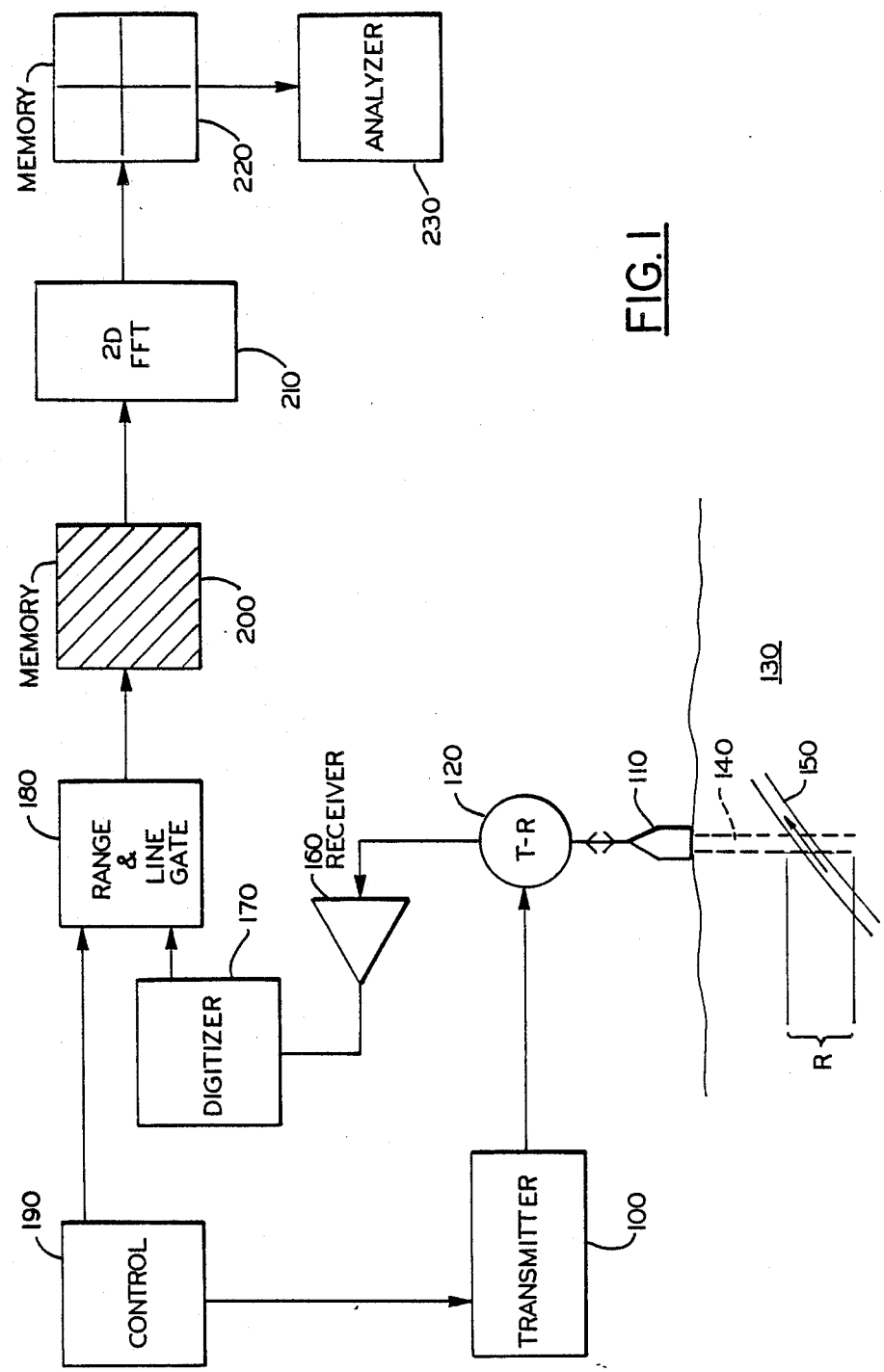
FIG. 1 is a block diagram of an ultrasound velocity measuring system.

FIG. 1 illustrates an ultrasound blood velocity measurement system which incorporates the invention. A transmitter 100 excites an ultrasound transducer 110 via a TR switch 120 to transmit broadband pulses of ultrasound energy into a body 130 along a narrow beam 140. The ultrasound energy in the beam is backscattered from structures in the body, for example from blood flowing in an artery 150, to produce echoes which return to and are detected by the transducer 110. The frequency of ultrasound echo signals scattered from structures of the body (moving in the direction of the axis of the beam 140) will be shifted with respect to the frequency of the ultrasound energy produced by the transducer in accordance with the Doppler equation. Echo signals produced by the transducer are coupled to a receiver 160 via the TR switch 120 and are amplified therein. The output of the receiver is connected to the a radio frequency digitizer 170 which extracts and digitizes samples of the echo signals. The output of the digitizer is connected to the input of a range and line gate 180.

Figure 2:
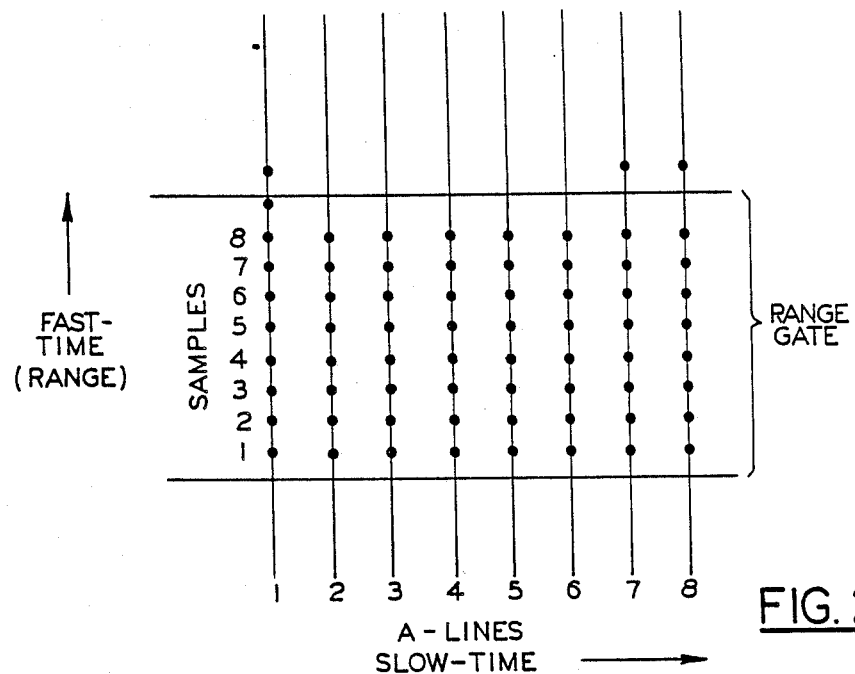
FIG. 2 illustrates the arrangement of data samples in an array.

Each transmitted RF pulse produces an echo A-line signal which maps range along the axis of beam 140 into signal arrival time. Control circuit 190 operates range gate 180 to select signal samples which originate within the region of the body defined by range R and the beam 140. The digitizer 170 periodically samples the RF signal of the A-line at a rate which is at least twice the frequency of the highest component in the signal. Successive samples which lie within the range R along each A-line are stored as a column vector of a matrix array in memory 200. Successive A-lines are stored at successive columns in the matrix so that each row of the matrix represents samples taken at corresponding ranges along successive A-lines. Individual elements stored in the matrix in memory 200 may thus be identified and addressed by a "fast-time" index (which identifies a sample along each A-line and thus a row of the matrix) in conjunction with a "slow-time" index (which identifies the specific A-line and thus the column in the matrix). FIG. 2 illustrates a matrix of data made up of signals from eight A-lines each of which includes eight signal samples within a range gate.

Satisfactory processing of ultrasound echo data obtained from a 45° scan of a human common carotid artery at an RF center frequency of 5 MHz and a PRF of 5 kHz using a 6 mm beam at a 3 cm focus was obtained with a range gate set to select 32 samples from each of 64 A-lines.

Figure 3A:
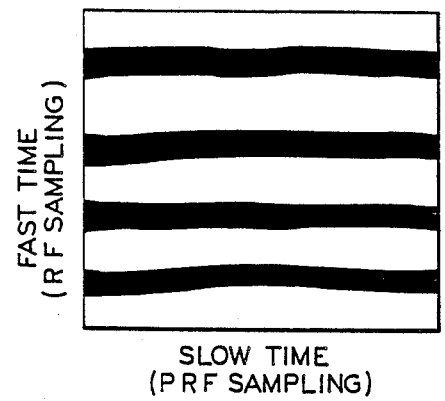
FIGS. 3a through 3c illustrate the effect of motion in the scattering medium on the values of data samples which are stored in an array.
Figure 3B:
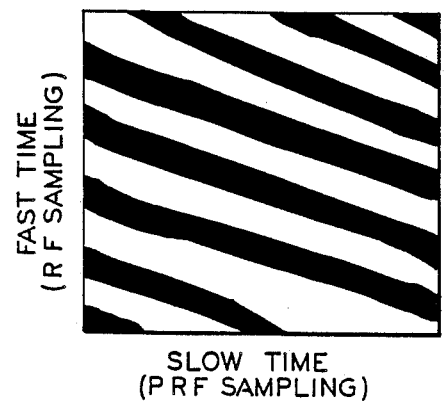
Figure 3C:
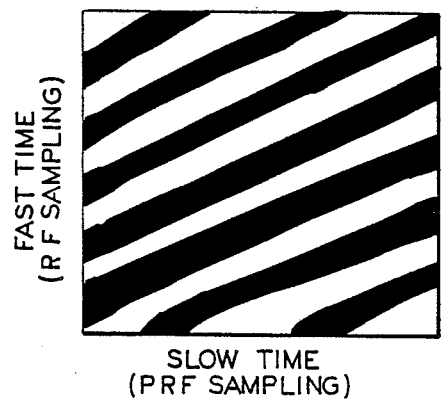

The above-mentioned prior art publication of the inventors Embree and Mayo teaches that data values stored within the matrix in memory 200 will exhibit fringing patterns which characterize motion within the region of interest of the body as illustrated in FIGS. 3a through 3c. In the figures, positive echo signals are displayed as white areas and negative signals as black areas. The bandpass nature of the ultrasonic transducer 100 makes the echo signal look like a series of alternate light and dark stripes. If the fixed transducer is pointed at a single blood vessel with constant flow, the flow at the center of the vessel will be greatest and will decrease to zero at the walls. FIG. 3a is typical of the signal from the vessel walls. The horizontal strips are typical of structures without velocity components along the beam axis. FIG. 3b illustrates signals typical of structures which are moving away from the transducer while FIG. 3c illustrates signals from structures which move towards the transducer.

The array stored in memory 200 is processed in a two-dimensional discrete Fourier transform processor 210 and the results are stored in a second memory 220. Depending on speed and data constraints of the system, the two-dimensional discrete Fourier transform processor 210 may either be accomplished as a software routine in a general purpose digital computer or microprocessor, or, alternatively, may be effected by dedicated fast Fourier transform processor chips.

The output of the discrete Fourier transform processor 210 is an array of data elements which represent the transform of the A-line sample data with respect to a first (slow-time) variable which identifies individual A-line vectors in the data set and a second (fast-time) variable which represents the discrete sample position along each A-line. The array in memory 220 may be interpreted as a two-dimensional frequency spectrum representation with respect to a fast-frequency variable $f_2$ which corresponds to the RF frequency spectrum of the received echo signals and a slow-frequency variable $f_1$ which corresponds to the Doppler frequency components.

Figure 4:
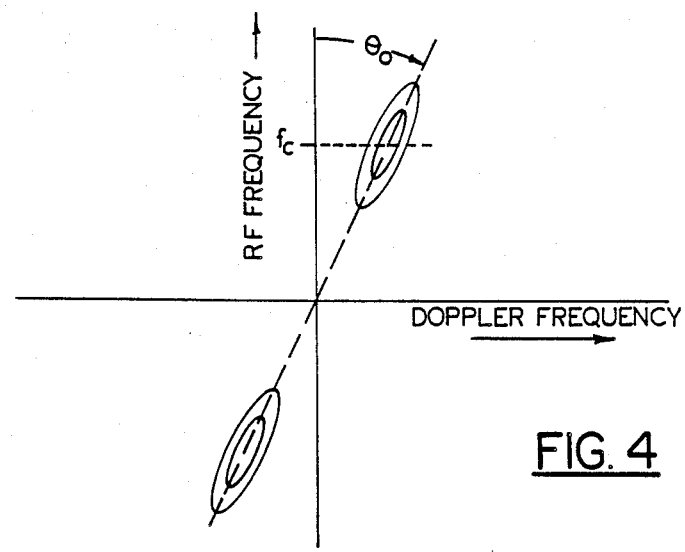
FIG. 4 illustrates a spectrum of typical Doppler signals in a two-dimensional Fourier frequency space.

The two-dimensional discrete Fourier transform data provides information about the velocity of the scattering medium in a region corresponding to the range gate. If the medium in the range gate is moving towards the transmitter with the velocity v then a contour plot of the magnitude of the two-dimensional discrete Fourier transform will have the general form shown in FIG. 4. For typical parameter values the major axis of the elliptical contours passes through the origin of the two-dimensional frequency plane making an angle $\theta_o$ with the vertical axis. In one embodiment of the invention the slope of the major axis may be determined from the ratio of the first moment of the signal spectrum to the total signal spectrum power and the mean velocity is calculated therefrom. Likewise the velocity variance can be calculated using the second moment of the spectrum.

In a preferred embodiment, the velocity spectrum of the Doppler signal is determined by radial projection in the two-dimensional Fourier frequency space. The angle, and hence the velocity, is estimated by computing the radial projection of the magnitude (or magnitude squared) of the two-dimensional Fourier transform $A(f_1, f_2)$ where $f_1$ is the Doppler frequency parameter and $f_2$ is the RF frequency parameter. The radial projection of the Fourier transform magnitude along radial direction, $\theta$, is $$S(\theta) = \int_o^\infty |A(r\sin(\theta), r\cos(\theta))| dr$$

Figures 5A, 5B:
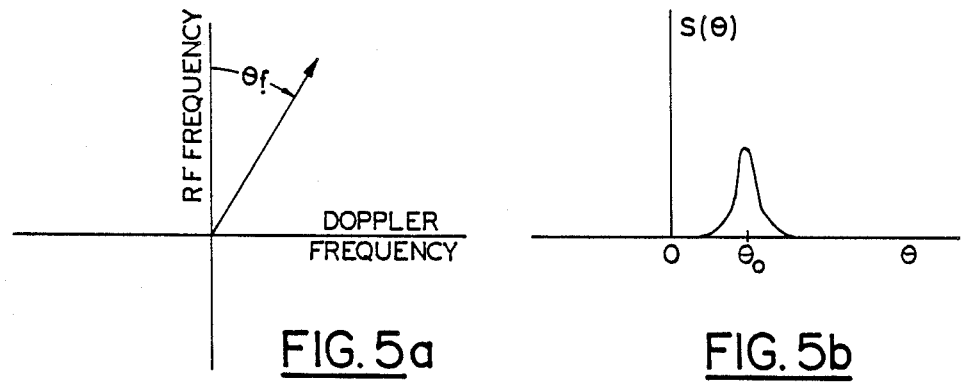
FIGS. 5a and 5b illustrate the geometry of a radial projection in two-dimensional Fourier frequency space.

The radial projection will have a maximum value of $\theta = \theta_o$, the angle associated with the velocity of the moving medium. FIG. 5a illustrates the radial projection geometry and FIG. 5b illustrates a typical plot of the radial projection.

Figure 6:
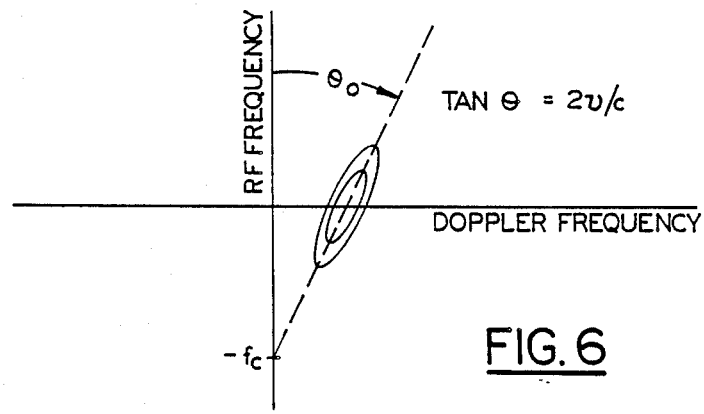
FIG. 6 illustrates a radial projection of the spectrum of a complex envelope of Doppler signals in two-dimensional Fourier frequency space.

In the preferred embodiment the two-dimensional Fourier transform is computed from the complex envelope of the A-lines rather than from the actual radio frequency echo signals. The complex envelope signal may be obtained from the RF samples using well known digital filtering techniques or the complex envelope signal can be sampled by using an analog complex envelope demodulator which is included in the receiver 160. The Fourier transform of the complex envelope is a shifted version of FIG. 4; the major axis of the elliptical contours intersects the fast frequency axis at $-f_c$ where $f_c$ is the center frequency of the transmitted ultrasound pulses (FIG. 6). Thus, when digitized samples of the complex envelope are utilized, the radial projection is centered on the point $(0, -f_c)$ in the two-dimensional Fourier frequency plane and if $A(f_1, f_2)$ is the Fourier transform of the complex envelope, the desired radial projection is given by $$S(\theta) = \int_o^\infty |A(r\sin(\theta), r\cos(\theta) - f_0)| dr$$

Figure 7:
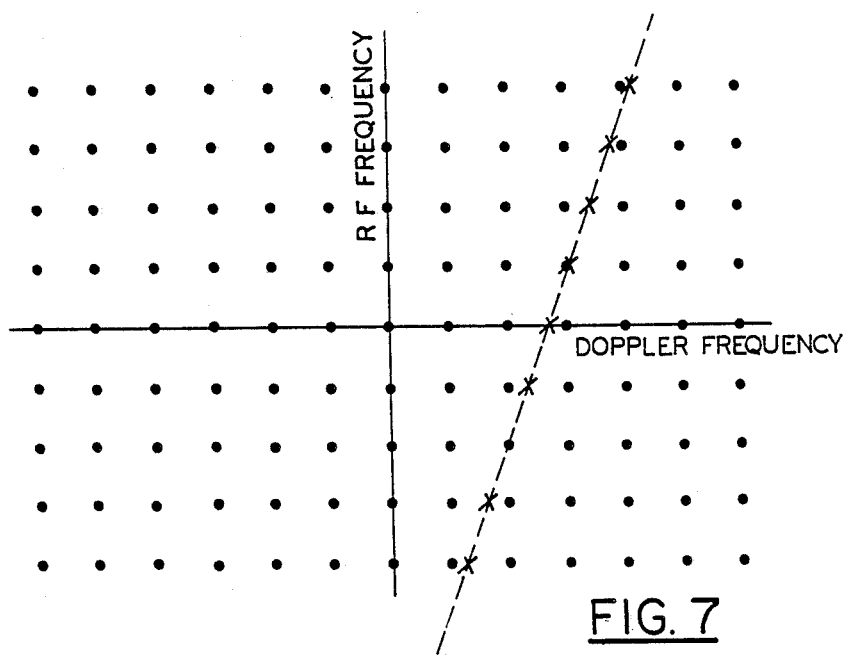
FIG. 7 illustrates the interpolation of two-dimensional discrete Fourier transform data values which are used to compute radial projections along an indicated line in two-dimensional Fourier frequency space.

Since the two-dimensional discrete Fourier transform only gives discrete sample values, in practice the integral is approximated by a sum of sample values along the projection line. The radial projection line generally does not pass directly through the discrete Fourier transform sample points, so that interpolation is required. FIG. 7 represents the two-dimensional Fourier transform plane; dots indicate the location of the sample points. The radial projection is approximated by summing interpolated sample values at the locations indicated by the stars. These interpolated values can be computed using a prior art interpolation algorithm. Simple linear interpolation between adjacent horizontal sample points give satisfactory results and is computationally efficient.

Figure 8:
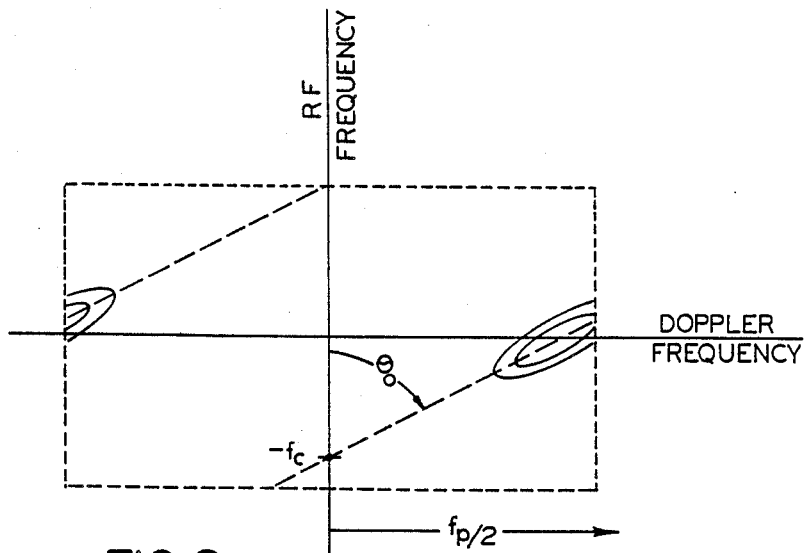
FIG. 8 is a contour plot of a two-dimensional Fourier frequency space which illustrates spectral "wraparound" at high velocities.

Because the discrete Fourier transform is periodic in nature, the two-dimensional spectrum wraps around a unit cell at high velocities as illustrated in FIG. 8. In order to continue to obtain good radial projections at high velocities, where the spectrum wraps around, it is necessary to wrap the projection line around the axes as illustrated in FIG. 8.

Appendix I is a MATLAB program which illustrates the computation of the radial projection from the magnitude squared of two-dimensional discrete Fourier transform of an A-line sample array.

Figure 9A:
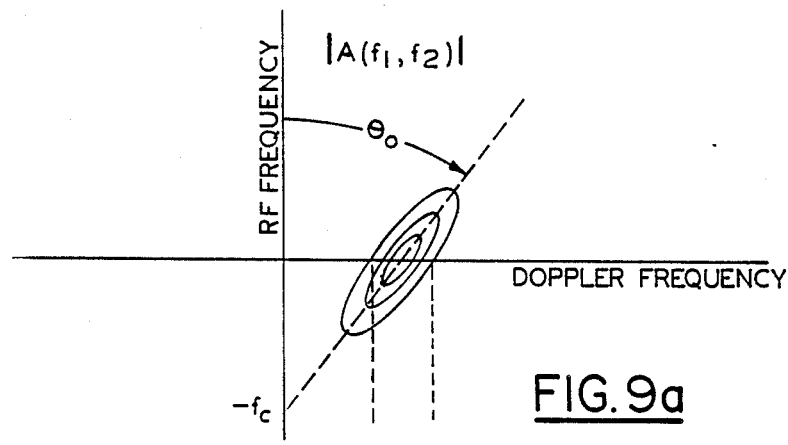
FIGS. 9a and 9b represent the extraction of conventional one-dimensional Doppler spectra in two-dimensional Fourier space.
Figure 9B:
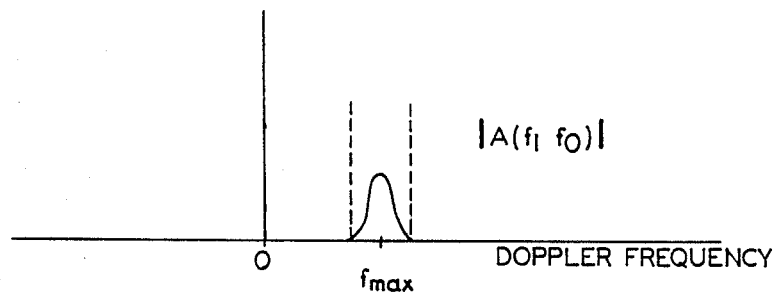

As noted above, in conventional Doppler processing of complex envelope data, each A-line is averaged over the range gate which collapses the data array into a single row with one complex sample for each A-line. Since averaging over the range gate is equivalent to only computing the zero frequency component of the discrete Fourier transform, the Doppler spectrum is simply a slice through the two-dimensional discrete Fourier transform along the slow frequency axis as illustrated in FIGS. 9a and 9b. Conventional Doppler processing thus wastes much of the information which is contained in the two-dimensional spectrum.

The radial projection technique of the invention may alternately be thought of as temporal frequency compounding. It is corresponds mathematically to a system which scales and then averages several independent conventional Doppler spectra taken at different center frequencies.

FIG. 10 contrasts the velocity spectra of blood flow in the common carotid artery of a human subject using the methods of the present invention with the prior art, using a data array consisting of 32 A-lines with a range gate containing eight complex samples (representing a range gate 1.2 mm long). FIG. 11 shows an example of velocity distribution as a function of range obtained using a radial projection. The vertical ridge down the center of the plot corresponds to regions outside of the artery where the velocity is zero. The profile of velocities within the artery are clearly visible. FIG. 12 is a display of the same quantities processed by prior art Doppler methods.

Although the methods of Doppler signal processing of the invention have been described herein with respect to a preferred embodiment for measuring blood flow velocities, the invention is not so limited and may find application in the processing of Doppler radar and sonar signals as well as direct Doppler frequency measurement techniques.

APPENDIX I

```
S=zeros(1,Nv);
U=ones(1,Nv);
k=1:Nv;
    alpha=alpha1+(k−1)*dalpha;
    for m=1:N2;
        m=m
        nr=alpha*(m−N2/2−1)*d2+fo)/d1+N1/2+1;
        n̂=floor(nr);
        delta=nr−n;
        n=mod(n−1,N1)+1;
        np1=n+1;
        np1=mod(np1−1,N1)+1;
        S=S+(U−delta).*A2(m,n)+delta.*A2(m,np1);
    end
    j=0:Nv−1;
```

What is claimed:

1. A method for measuring velocity components of a fluid within a region of an object, comprising the steps of:
   transmitting a periodic train of pulses of ultrasound energy in a single direction through the region of the object;
   receiving echo signals which represent echoes of said pulses which are back-scattered from said region;
   sampling the amplitude of said received signals using a sampling frequency which is greater than twice the highest frequency of the echoes;
   taking a two dimensional discrete Fourier transform of said samples with respect to a first fast-time variable which measures sampling periods, and a second slow-time variable which measures pulse repetition periods, whereby the echo signals from the moving fluid are mapped as an ellipse into a two-dimensional Fourier frequency space; and
   determining velocity components in said region, along the propagation direction of said ultrasound energy by measuring the angle between the major axis of said ellipse and coordinate axes of said Fourier frequency space.

2. A method for measuring velocity components of a fluid within a region of an object, comprising the steps of:
   transmitting a periodic train of pulses of ultrasound energy in a single direction through the region of the object;
   detecting signals which represent echoes of said pulses which are back-scattered from said region;
   sampling said detected signals using a sampling frequency which is greater than twice the highest frequency of ultrasound energy;
   taking a two dimensional Fourier transform of said detected signals with respect to a first fast-time variable which measures sampling periods and a second slow-time variable which measures pulse repetition periods, whereby the samples of the detected signals are mapped into a two-dimensional Fourier frequency space;
   calculating a radial projection of said mapped signals in said Fourier frequency space; and
   calculating Doppler shifts which said fluid causes in said echoes by analysis of the waveshape of said radial projection.

3. The method of claim 1 or 2 wherein the step of taking the two-dimensional transform comprises taking a two-dimensional Fourier transform of samples of the complex envelope of the detected signals.

4. In a velocity measuring system of the type wherein a finite number of periodic pulses of a wave are sampled and a set of the wave samples is analyzed to determine Doppler shifts, wherein samples of each pulse are measured at a rate which is higher than twice the highest frequency in the pulses, the improvement comprising the steps of:
   taking a two-dimensional Fourier transform of the set of samples with respect to a first fast-time variable which measures the sampling period and to a slow-time variable which measures the interpulse period, whereby the sample set is mapped into a Fourier frequency space wherein constant Doppler shifts are mapped as radial lines; and
   analyzing said transformed sample set along said radial lines to extract Doppler shift information therefrom.

5. The method of claim 4 wherein the step of analyzing said transformed sample set comprises taking a radial projection of said sample set.

6. Apparatus for measuring the velocity of a moving fluid in a region of an object comprising:
   means for periodically transmitting pulses of RF frequency ultrasound energy in a single direction through said region;
   means for detecting echoes of a finite number of said pulses which are back scattered from said region and which generate signals representative thereof;
   means for extracting a finite group of signal samples from the echoes of each of the pulses in said set;
   means for computing a two-dimensional Fourier transform of said signal samples with respect to a fast-time variable which measures the FR frequency of said samples and to a second slow-time variable which measures the periods of said pulse trains, whereby the samples are mapped into a two-dimensional Fourier frequency space wherein constant Doppler shifts are mapped as radial lines; and means for analyzing the transformed signal samples along radial lines in said Fourier frequency space to determine Doppler shifts in caused by fluid motion in said region.

7. The system of claim 6 wherein the means for analyzing the transformed signals comprise means for computing a radial projection of said transformed signals in said Fourier frequency space.

8. The system of claim 7 further comprising suppressing alias signals by computing a radial projection along radial lines which wrap around unit cells in the Fourier frequency space.

9. The system of claims 6 or 7 further comprising means for detecting the complex envelope of the signal representative of the echoes and wherein the means for extracting function by sampling the complex waveform of the echoes.

10. A method for processing discrete samples of pulsed wave signals to determine a velocity of a target comprising:

transforming the signal samples using a discrete two dimensional Fourier transform which maps a spectral components of a constant velocity Doppler shift into radial lines.

11. A method for processing discrete samples of pulsed wave signals to determine velocity of a target comprising the steps of:

transforming the signal samples using a discrete two dimensional Fourier transform which maps spectral components of a constant velocity Doppler shift into radial lines and taking a radial projection of the transformed signal samples to extract a velocity spectrum.

12. A method for processing discrete samples of pulsed wave signals to measure a characteristic of the velocity of a target comprising the steps of:

transforming the signal sample from a discrete two dimensional Fourier transform to produce a two dimensional Fourier spectrum;

extracting moments of the two dimensional Fourier spectrum directly and then calculating a characteristic of the velocity of the target therefrom.

13. The method of claim 12 wherein the parameter is mean velocity.

14. The method of claim 12 wherein the parameter is velocity variance.

15. A method for determining the velocity of an object from frequency shifts in waves received from the object comprising the steps of:

determining a plurality of individual Doppler spectra, taken at different center frequencies from said received waves, scaling said individual spectra; and averaging said scaled spectra.

16. The method of claim 15 wherein said received waves are ultrasound pulse echoes.

* * * * *